United States Patent
Bürgisser

[11] Patent Number: 5,193,403
[45] Date of Patent: Mar. 16, 1993

[54] PIPETTING DEVICE

[75] Inventor: Ernst Bürgisser, Zeiningen, Switzerland

[73] Assignee: EPR Labautomation AG, Rheinfelden, Switzerland

[21] Appl. No.: 455,460

[22] PCT Filed: Feb. 21, 1989

[86] PCT No.: PCT/CH89/00033
§ 371 Date: Nov. 29, 1989
§ 102(e) Date: Nov. 29, 1989

[87] PCT Pub. No.: WO89/10191
PCT Pub. Date: Nov. 2, 1989

[30] Foreign Application Priority Data
Apr. 18, 1988 [CH] Switzerland ............ 1419/88

[51] Int. Cl.⁵ .................................................. G01N 1/14
[52] U.S. Cl. .................................................. 73/864.17
[58] Field of Search ............ 73/863.32, 864.11–864.18, 73/864.22; 436/180; 422/100; 222/309, 135, 136

[56] References Cited
U.S. PATENT DOCUMENTS

| 720,492 | 2/1903 | Sedberry | 222/309 |
|---|---|---|---|
| 2,172,575 | 9/1932 | Caulfield | 73/864.15 |
| 3,184,122 | 5/1965 | Nerenberg | 222/309 |
| 3,572,552 | 3/1971 | Guinn | 73/863.32 |
| 3,712,794 | 1/1973 | Farr | 422/100 |
| 3,754,863 | 8/1973 | Reunanen | 422/100 |
| 4,091,677 | 5/1978 | Oshikubo | 73/864.15 |
| 4,106,911 | 8/1978 | Marcelli | 23/259 |
| 4,158,035 | 6/1979 | Haase et al. | 422/100 |
| 4,494,677 | 1/1985 | Falcoff | 73/864.16 |
| 4,532,805 | 8/1985 | Flesher | 73/863.32 |
| 4,621,665 | 11/1986 | Webb | 141/1 |
| 4,640,297 | 2/1987 | Bates | 73/864.13 |
| 5,021,217 | 6/1991 | Oshikubo | 73/863.32 |

FOREIGN PATENT DOCUMENTS 0158852 10/1985 European Pat. Off. .
0215536 3/1987 European Pat. Off. .
0206945 2/1988 European Pat. Off. .

Primary Examiner—Robert Raevis
Attorney, Agent, or Firm—Walter C. Farley

[57] ABSTRACT

An automated pipetting device has a first driving motor (1) with a spindle (1') to drive a plurality of injection pistons (6) each movable by a piston shaft (7), and a second driving motor (2) that drives a carrier plate (3) with a spindle (2') in a horizontal direction. A plurality of pipette cylinders (5) are carried in the carrier plate (3) which is pressed against a stationary valve plate (4). The valve plate has a duct system (10) with channels (11,12,13) for supplying and removing liquid. Each individual pipette is spring biased so that its outlet region is pressed against the valve plate at openings of the channels and the carrier and pipettes can be moved with the pipette outlets pressed against the valve plate surface. Each pipette has independent means for applying the spring bias.

10 Claims, 2 Drawing Sheets

PIPETTING DEVICE

FIELD OF THE INVENTION

This invention is in the filed of analytical laboratory equipment and relates to a dosing device with a plurality of simultaneously operable dosing pumps, preferably pipettes, which are operated with a piston or plunger.

BACKGROUND OF THE INVENTION

The automation of dosing processes requires dosing pumps which are particularly suitable for automation and of which hitherto a central position has been occupied by piston or plunger dosers. However, hose squeezing pumps have also been used for dosing purposes, together with displaceable dosing channels with which part of the liquid column can be separated. All these dosing pumps are used in arrangements comprising several of them so as, e.g., to be able to simultaneously take up and/or supply a plurality of identical volumes. Frequently the pump has to be washed out and filled with another liquid, which requires the use of valves enabling these processes to be controlled and automated.

However, this involves a larger number of simultaneously operating dosing pumps to be used in an arrangement with a minimum amount of space available requiring a large number of parts all acting within a small area. An example is the loading or charging of a microtitre or microtest plate (MTP).

The MTP has been established as an industrial standard in clinical routine diagnosis and in research. It is generally a plastic disposable article with 96 depressions or cavities, which can be used in place of small test tubes for receiving test reagents. The 96 cavities are arranged in a rectangular matrix of $120 \times 80$ mm and are spaced by only 9 mm from one another. As a function of the geometry of the cavities, a MTP is suitable for receiving a few microlitres and up to as much as approximately 1 milliter. Thus, the function of automatic dosing is to simultaneously deal with these 96 cavities, which requires 96 dosing pumps with their valves.

For manipulating reagents in connection with microtest plates e.g. multichannel pipettes (8 or 12) or automatic pipetting devices (8 or 12) are known. However, such devices have a capacity limit, which leaves much to be desired. The problem is how is it possible to supply and/or remove liquids with respect to a microtitre plate more rapidly than hitherto and with great accuracy.

SUMMARY OF THE INVENTION

An object of the present invention is to provide an apparatus for delivering liquids to an extracting liquids from a microtitre plate automatically, quickly and with great accuracy.

Briefly described, the invention comprises an apparatus for dosing liquid comprising a plurality of pipettes each having a piston and a piston rod for operating the piston and a first motor drive coupled to the piston rods for reciprocally driving the rods parallel with a first, preferably vertical, axis. A carrier plate supports the plurality of pipettes with an outlet of each pipette exposed at a surface of the carrier plate. A stationary valve plate has a second surface facing, generally parallel with an adjacent to the first surface of the carrier plate, the valve plate having an arrangement of channels for conveying fluid to and from the pipette outlets, the channels including a plurality of channel openings at the second surface. A second motor drive is coupled to the carrier plate for positioning the carrier plate relative to the valve plate. Each pipette outlet is independently urged into sealing contact with the valve plate so that substantially leak-free connections are formed between the pipette outlets and the channel openings.

BRIEF DESCRIPTION OF THE DRAWINGS

The invention is described in greater detail hereinafter with reference to non-limitative embodiments shown in and the attached drawings, wherein.

DESCRIPTION OF THE PREFERRED EMBODIMENTS

Figure 1:
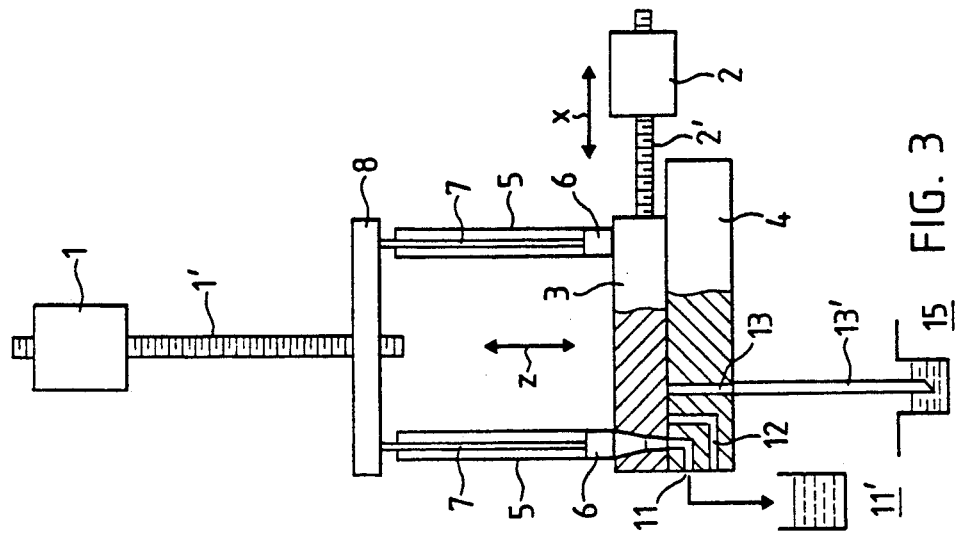
FIG. 1 is disemplified schematic view of a device according to the invention in a first operative position.
Figure 2:
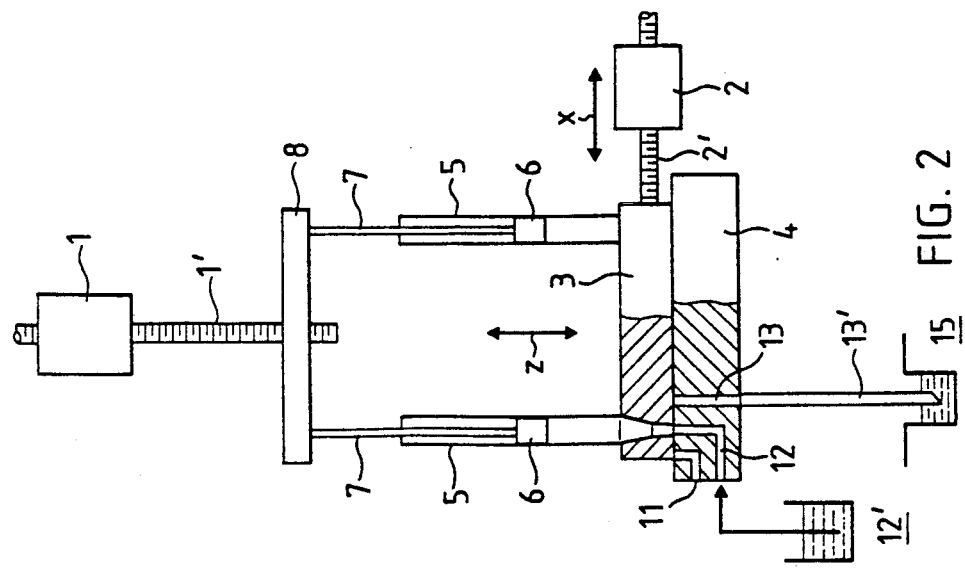
FIG. 2 is a schematic view of the device of FIG. 1 in a second operative position.
Figure 3:
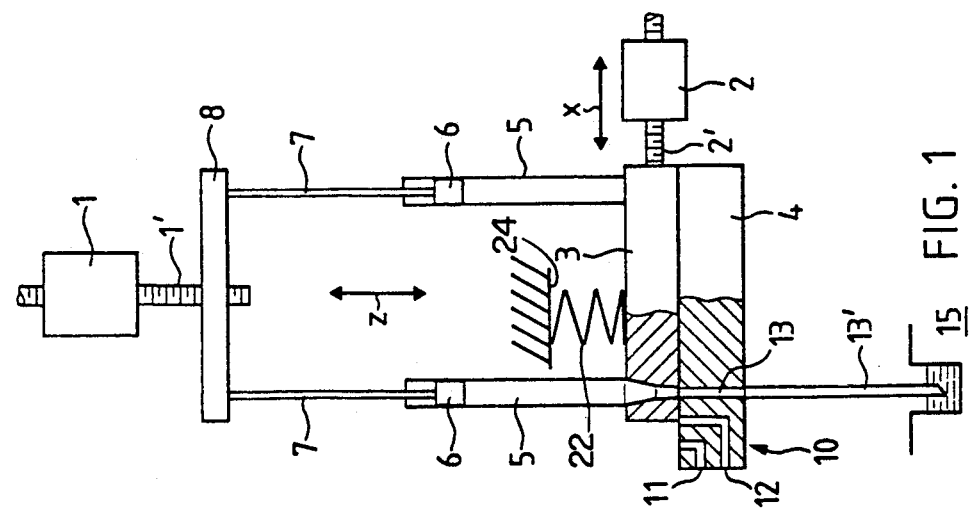
FIG. 3 is a schematic view of the device of FIG. 1 in a third operative position.

FIGS. 1 to 3 show the same embodiment in three different working positions, namely, FIG. 1 shows suction and mixing in a MTP; FIG. 2 shows suction from a storage container, dispensing and washing; and FIG. 3 shows discharge into a collecting tank. The different working positions are brought about by the displacement of equipment parts. One of a plurality of similar valve function on a pipette is shown and these are all simultaneously operable. An additional pipette is shown. There are in fact 96 of these in the present embodiment, which lead to a homologous array corresponding to the cavities of a microtitre plate.

The device essentially comprises a first motor drive 1 which by means of a spindle 1' drives a plurality of injector or syringe pistons 6 displaceable by a piston rod 7, preferably in the vertical direction z. A carrier plate 3 is displaced by means of a second motor drive 2, via a spindle 2' and preferably in the horizontal direction. A fixed valve plate 4 with a channel system 10 constituted by channels 11, 12 and 13 and a plurality of pipette cylinders 5 is provided, being arranged in the carrier plate 3 in a manner to be described hereinafter.

In the present embodiment there are 96 pipettes and 3 channels of the channel system 10 are associated with each pipette, i.,e. the, valve plate 4 has 288 inlets in its side facing carrier plate 3, which inlets can be brought into operative connection with the pipettes by displacement of the carrier plate. Channel system 10 comprises reagent supply channel 12 (to all 96 pipettes), discharge channels 11 (for all 96 pipettes) and channels 13 for operating the MTP cavities (for all 96 pipettes). The operating channels 13 continue on e.g. in the form of a hollow needle 13' which can be introduced into the MTP cavity. Seen from below the device has a relatively large number of points, 96 needles arranged in the MTP array project from the valve plate. The microtitre plates are delivered to these needles for processing. In place of the hollow needles for the continuation 13' of channels 13 it is possible to use commercially available disposable plastic syringes, which can when necessary be replaced The replacement of such plastic syringes can take place automatically by means of a perforated plate-like device with inserted new syringes, which are inserted in the MTP supply means.

The drawings which only show the principle of the invention do not show:

a control for the first and second motor drives, which naturally operate alternately, the first drive drawing up and emptying the pipettes, preferably constituted by commercially available syringes and the second drive moves the carrier plate between one of the three positions;

such a control is e.g. incorporated into an analytical program by means of micorporcessor software;

guide means for the carrier plate, which e.g. only permits a specific push/pull movement in the x-direction;

rigid fastenings, e.g. between the first drive 1 and the carrier plate 3;

the baseplate and casing firmly connected to the second drive 2 and valve plate 4;

a lifting device for supplying a microtitre plate 15 to the cannula of the device; and all the supply 12 and removal 11 channels of the channel system 10 in valve plate 4.

The channel system 10 is formed by a network of bores passing through the valve plate 4 at right angles to one another, preferably in the manner of a chessboard and in two planes (for filling and discharging). The connections to the 96 inlets issue into the bores and it is possible to arrange two bore networks so that each set of vertical bores issues into a common outlet i.e., a single horizontal bore any other production-caused openings to the network are closed. Several tapping points on either network can be brought together outside the same to form a common inlet or outlet.

In operation, all the channel parts are filled with liquid and free from air bubbles. Advantageously the starting operation is a filling stroke through the supply channel 12 and a subsequent ejection through discharge channel 11 until the channel system is free from bubbles. Filling can also be commenced with a filling stroke through the cannulas 13, so that the path to each cassette is of the same length, i.e. the same volume per stroke is drawn into the pipettes. Subsequently by changing over to one of the two networks the channel system is filled and the air ejected.

Sealing problems which can only be solved according to the invention result from a bidimensional arrangement of 288 inlets in one and 96 supply means in the other plane. These planes must move relative to one another and assume exact positions. All operated 96 connections must reliably operate, because if only a single connection fails the MTP system is rejected.

Figure 4:
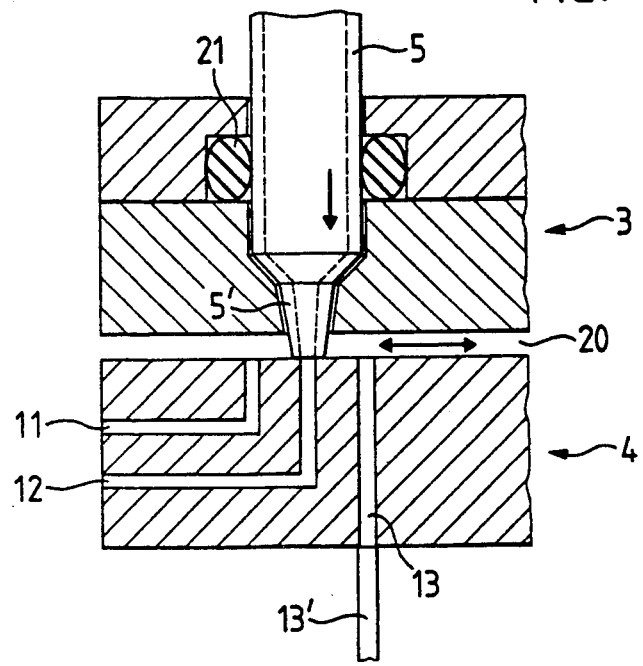
FIG. 4 is a partial sectional view of a structure according to the invention.
Figure 5:
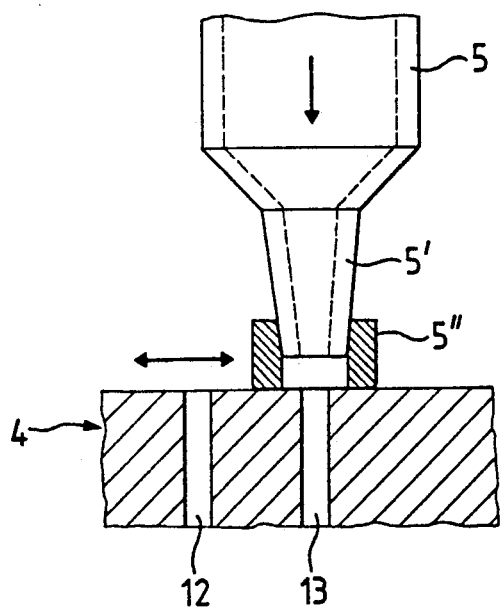
FIG. 5 is a partial sectional view of a further embodiment of the invention.

FIG. 4 deals with this problem. It is very difficult to keep two displaceable plates on one another in such a way that they have the same sealing effect at all points. For sealing purposes pressure must be exerted on the sealing faces. When pressure is applied, there is a slight deformation of the plates, which can cause leaks. In the case of an arrangement of 288 points to be sealed in a 12×8 cm array, analysis can be ruined by a leak. Thus, the plate-to-plate sealing problem has been obviated and instead each pipette provides for its own sealing. The collective sealing of 96 pipettes has been changed to individual sealing thereof, so that the hitherto necessary requirement, only achievable with great expense, of parallelism of the transfer planes with increasing risks with increasing surface areas has been converted into an easily attainable transfer solution with greatly reduced risk.

At its outflow point, each pipette is supported on the valve plate with the necessary spring tension with the valve orifices and, if necessary, moved under this spring tension on the transverse surface. The parallelism of valve plate and support plate is irrelevant and local sealing problems between the pipette outlet and the valve plate can be solved with limited effort and expenditure.

FIG. 4 shows how this can be achieved. The surface with three openings for channels 11, 12, 13 of valve plate 4 and the syringe nozzle 5' of pipette 5 in the carrier plate 3 form a transfer zone in transfer gap 20. The double arrow in the latter shows the displacement movement with which the nozzle 5' is moved from one inlet to the other. The nozzle 5' is pressed with an adequate force on to the valve plate 4 by means (springs, elastomer, etc.), which can exert this force. FIG. 4 shows an O-ring 21 fixed in the carrier plate in frictional engagement with respect to the pipette cylinder and its elastic force during the deformation (i.e. prestressing) of the O-ring presses the nozzle 5' against valve plate 4. This is indicated by the small, downwardly directed arrow in the cylinder. Another procedure for achieving spring action comprises exposing the pipette cylinder to a spring tension at the upper end opposite to nozzle 5', in that e.g. a helical compression spring is made to press on to the top part of the cylinder by means of a support plate fixed to the carrier plate 3. The cylinders can also be pressed downwards by an elastic mat with holes for the passage of the pistons wherein uniformly distributed pins located on the common plate are pressed on to the mat.

When using commercially available plastic syringes as pipettes, then a Teflon sealing ring 5" or the like can be mounted on the nozzle 5'. The sliding friction of such a sealing ring is small and the sealing action very satisfactory, while the price is negligible. The simplicity of the construction allows tolerance for "individual" zone seals with regards to material and shaping.

During assembly of the device, the carrier plate 3 with the array of pipettes, which are resiliently mounted and project slightly downwards out of the carrier plate, is mounted on the base-fixed valve plate and pressed by means of e.g. four gas pressure springs located in the corners of the carrier plate. Deformation of the plate no longer impairs the sealing, because this is compensated by the vertical clearance of the pipettes. Such an arrangement can easily be dismantled, in order to e.g. replace the pipette or syringes by new ones. The presence of this spring force is schematically indicated in FIG. 1 by a compression coil spring 22 acting between the upper surface of carrier plate 3 and a fixed surface 24 to urge the carrier plate against the valve plate.

It is so possible in this way to obtain arrangements with more than 96 pipettes. The aforementioned number is of interest, because microtitre plates have 96 cavities. Hitherto there has been no simple, inexpensive, effective and tight pipetting device able to simultaneously handle all 96 cavities, which was naturally a considerable obstacle to automation.

Thus, the device essentially has a first motor drive 1 which drives, preferably vertically, by means of a spindle 1' a plurality of syringe pistons 6 displaceable on a piston rod 7 and a second motor drive 2, which preferably horizontally drives a carrier plate 3 by means of a spindle 2'. On a fixed valve plate 4 with a channel system 10 constituted by channels 11, 12, 13 for the supply and removal of liquid is arranged a carrier plate with a plurality of pipette cylinders 5 arranged in said plate and pressed by the spring tension of means 21 against the pipettes. On the outlet side, each pipette is supported with spring tension on the valve plate with valve orifices and under this spring tension is, if necessary, moved on the transfer surface. Each pipette has means, such as springs, elastic rings and the like for exerting such a spring tension. The carrier plate 3 is pressed by spring tension onto the valve plate in opposition to the counterpressure of the spring means of the individual pipettes. This can e.g. be brought about by gas pressure springs. The spring tension on the carrier plate is made higher than the sum of all the spring tensions of the individual pipettes. Thus, e.g. each pipette is pressed on to the valve plate with a spring tension of 600 g, which gives an overall pressure of nearly 60 kg. The gas pressure springs are then chosen in such a way that they enable a pressure of 80 to 100 kg to be exerted on the carrier plate.

What is claimed is:

1. An apparatus for dosing liquid comprising the combination of
    a plurality of pipettes (5) each having a piston (6) and a piston rod (7) for operating said piston;
    a first motor drive (1, 1', 8) coupled to said piston rods for reciprocally driving said rods parallel with a first axis (Z);
    a carrier plate (3) supporting said plurality of pipettes with an outlet of each pipette exposed at a first surface of said carrier plate;
    a stationary valve plate (4) having a second surface facing, generally parallel with and adjacent to said first surface of said carrier plate, said valve plate having channel means for conveying fluid to and from said pipette outlets, said channel means including a plurality of channel openings at said second surface;
    a second motor drive coupled to said carrier plate for positioning said carrier plate relative to said valve plate; and
    means for independently urging each said pipette outlet into sealing contact with said valve plate, whereby substantially leak-free connections are formed between said pipette outlets and said channel openings of said channel means.

2. An apparatus according to claim 1 wherein said channel means includes a set of channel openings for each pipette, each said set including three openings for supply and removal of liquids.

3. An apparatus according to claim 2 wherein each said pipette includes a nozzle portion protruding through said first surface of said carrier plate and contacting said second surface of said valve plate, each said nozzle forming a transfer zone movable from one to another of said channel openings as said carrier plate is positioned by said second motor drive.

4. An apparatus according to claim 1 wherein each said pipette outlet includes a nozzle portion protruding through said first surface of said carrier plate and contacting said second surface of said valve plate, each said nozzle forming a transfer zone movable from one to another of said channel openings as said carrier plate is positioned by said second motor drive.

5. An apparatus according to claim 4 wherein each said means for urging includes an elastomeric body urging said nozzle toward said second surface.

6. An apparatus according to claim 4 wherein each said pipette is a plastic syringe, said apparatus including a low-friction sealing ring around each said nozzle in a position to contact said second surface.

7. An apparatus according to claim 1 wherein each said means for urging includes an elastomeric body urging said pipette outlet toward said second surface.

8. An apparatus according to claim 1 wherein said plurality of pipettes are arranged in said carrier plate in a uniform orthogonal array.

9. An apparatus according to claim 8 wherein said array includes spacing between said pipettes corresponding to the spacing between cavities in a microtitre plate.

10. An apparatus according to claim 9 and including means for pressing said carrier plate toward said valve plate with a force greater than the sum of forces exerted by all of said means for urging said pipettes.

* * * * *